United States Patent
Baek et al.

(10) Patent No.: US 7,734,004 B2
(45) Date of Patent: Jun. 8, 2010

(54) GAIN CORRECTION FOR A CT SYSTEM

(75) Inventors: Jongduk Baek, Palo Alto, CA (US);
Norbert J. Pelc, Los Altos, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 318 days.

(21) Appl. No.: 11/851,609

(22) Filed: Sep. 7, 2007

(65) Prior Publication Data
US 2009/0067569 A1    Mar. 12, 2009

(51) Int. Cl.
*A61B 6/00* (2006.01)
(52) U.S. Cl. .................................................. 378/4
(58) Field of Classification Search .................. 378/4
See application file for complete search history.

(56) References Cited

U.S. PATENT DOCUMENTS 4,792,900 A * 12/1988 Sones et al. ............... 600/407
5,602,891 A *  2/1997 Pearlman .................. 378/62
5,774,519 A *  6/1998 Lindstrom et al. .......... 378/18

OTHER PUBLICATIONS

Mazin et al., 2D simulations of an inverse-geometry volumentric CT system with multiple detector arrays, Medical Imaging, Proceedings of SPIE, vol. 5745, 2005, pp. 889-897.*
Gilat et al., "Three-dimensional reconstruction algorithm for a reverse geometry volumetric CT system with a large array scanned source", Medical Imaging 2003: Physics of Medical Imaging, Proc. SPIE 5030, pp. 103-111, 2003.
Baek et al., "Two-dimensional reconstruction algorithm of an inverse-geometry volumetric CT system", Poster presented at the SPIE Conference in Feb. 2007.
Baek et al., "Two-dimensional reconstruction algorithm of an inverse-geometry volumetric CT system", Proceedings of SPIE Medical Imaging 2007: Physics of Medical Imaging, vol. 6510, 9 pages, Mar. 2007.

* cited by examiner

*Primary Examiner*—Edward J Glick
*Assistant Examiner*—Alexander H Taningco
(74) *Attorney, Agent, or Firm*—Beyer Law Group LLP

(57) ABSTRACT

A method for imaging unknown objects in a computed tomography (CT) system, comprising determining ray gain for a known object is provided. A CT reconstruction is performed with the known object to obtain reconstructed values. Ideal values are obtained for pixels of the known object. An error related to a difference between the reconstructed values and the ideal values is generated. A ray gain is estimated that reduces the error.

20 Claims, 7 Drawing Sheets

Single Detector Array

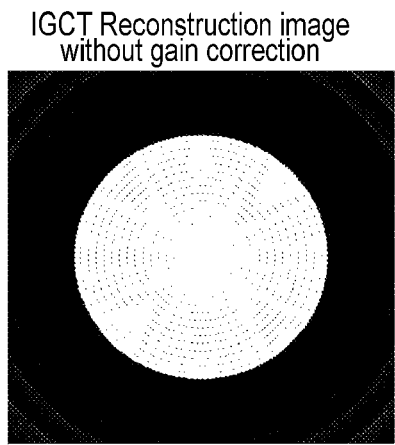
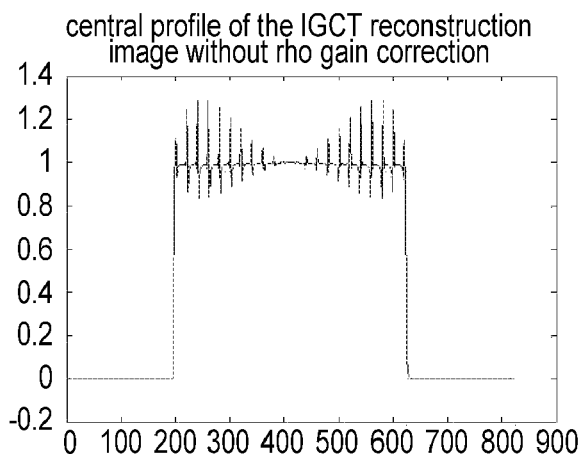
FIG. 4a          FIG. 4b
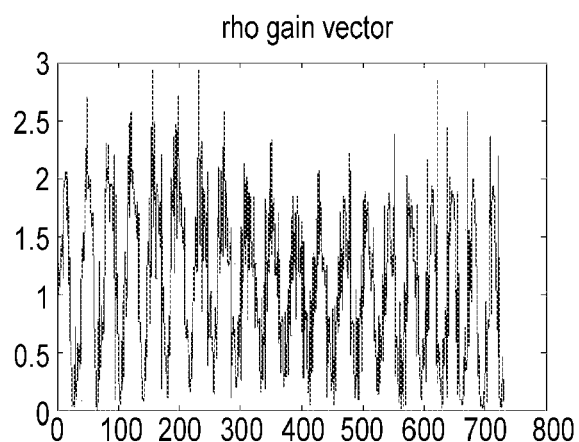
FIG. 4c
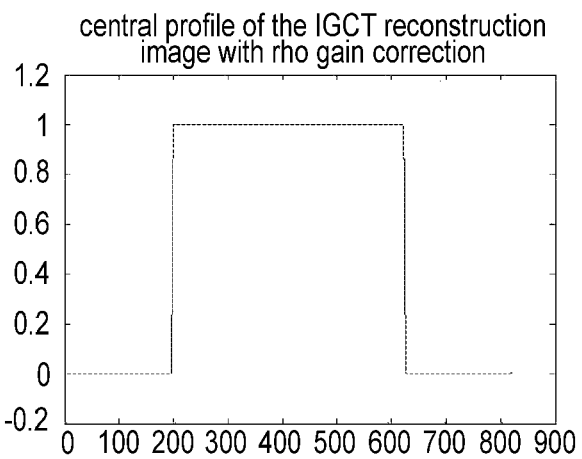
FIG. 4d

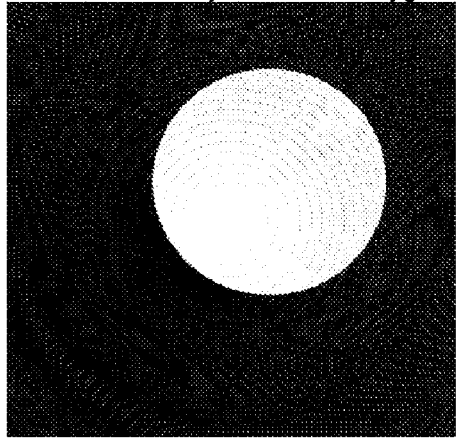
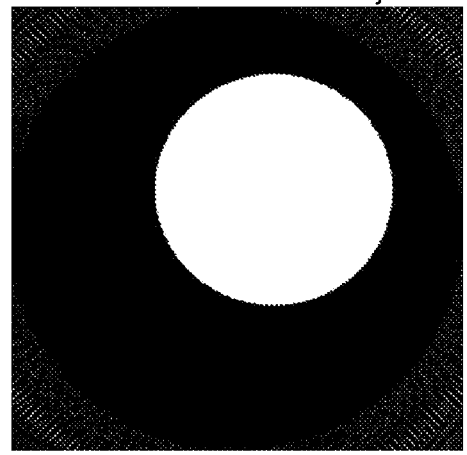
FIG. 6a  FIG. 6b
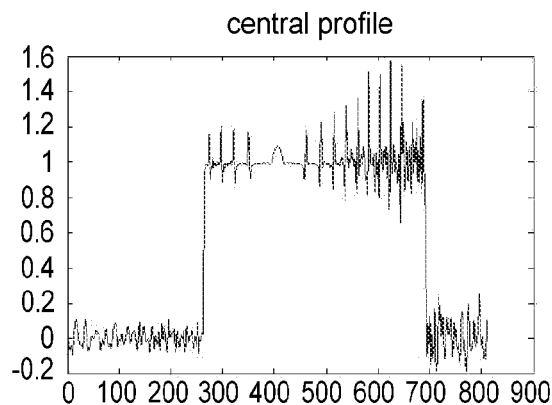
FIG. 6c
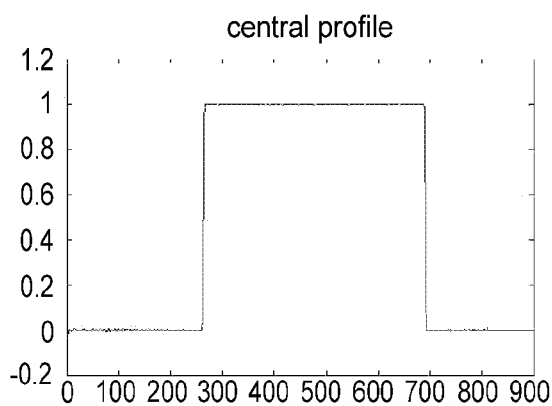
FIG. 6d

GAIN CORRECTION FOR A CT SYSTEM

BACKGROUND OF THE INVENTION

This invention relates generally to x-ray imaging including computed tomography (CT). More specifically the invention relates to a reconstruction algorithm for creating a CT image. Computed tomography (CT) is a medical technique for visualizing internal organs with high resolution. Both fan beams and cone beams of x-rays may be employed in CT.

SUMMARY OF THE INVENTION

In accordance with the invention, a method for imaging unknown objects in a computed tomography (CT) system, comprising determining ray gain for a known object is provided. A CT reconstruction is performed with the known object to obtain reconstructed values. Ideal values are obtained for pixels of the known object. An error related to a difference between the reconstructed values and the ideal values is generated. A ray gain is estimated that reduces the error.

In another manifestation of the invention, a computed tomography (CT) system is provided. A detector array is provided. An x-ray source array is provided. A display is provided. A controller receives data from the detector array and controls the display. The controller comprises at least one processor and computer readable media. The computer readable media comprises computer readable code for performing CT reconstruction with a known object to obtain reconstructed values, computer readable code for obtaining ideal values for pixels of the known object, computer readable code for generating an error related to a difference between the reconstructed values and the ideal values, computer readable code for estimating a ray gain that reduces the error, computer readable code for acquiring CT data for the unknown object, computer readable code for reconstructing a CT image of the unknown object by using the estimated ray gain, and computer readable code for displaying the CT image on the display.

The invention and objects and features thereof will be more readily apparent from the following detailed description and appended claims when taken with the drawings.

BRIEF DESCRIPTION OF THE DRAWINGS

FIG. 4a is an image with ringing artifacts.

FIG. 4b is a central profile in FIG. 4a.

FIG. 4c shows the gain vector for the offset 20-detector IGCT geometry.

FIG. 4d shows a central profile after applying the gain vector.

FIG. 6a shows a reconstructed image before applying the gain vector.

FIG. 6b shows a reconstructed image after applying the gain vector.

FIG. 6c shows the central profile of the reconstructed image before applying the gain vector.

FIG. 6d shows the central profile of the reconstructed image after applying the gain vector.

DETAILED DESCRIPTION OF ILLUSTRATED EMBODIMENTS

An inverse geometry volumetric CT (IGCT) system uses a large source array opposite a smaller detector array. 2D IGCT reconstruction may be performed by using gridding. One application of the present invention is 2D IGCT reconstruction without gridding. The IGCT raw data can be viewed as being composed of many fan beams, each with a detector at its focus. Each projection is undersampled but the missing samples are provided by other views. In order to get high spatial resolution, zeros are inserted between acquired projection samples in each fan beam, and reconstruction is performed using a direct fan beam reconstruction algorithm. Initial IGCT reconstruction results showed ringing artifacts caused by the fact that the rho samples in the ensemble of views are not equally spaced. An example of the invention provides a method for correcting the errors that reduces the artifacts to below one Hounsfield Unit.

Figure 1:
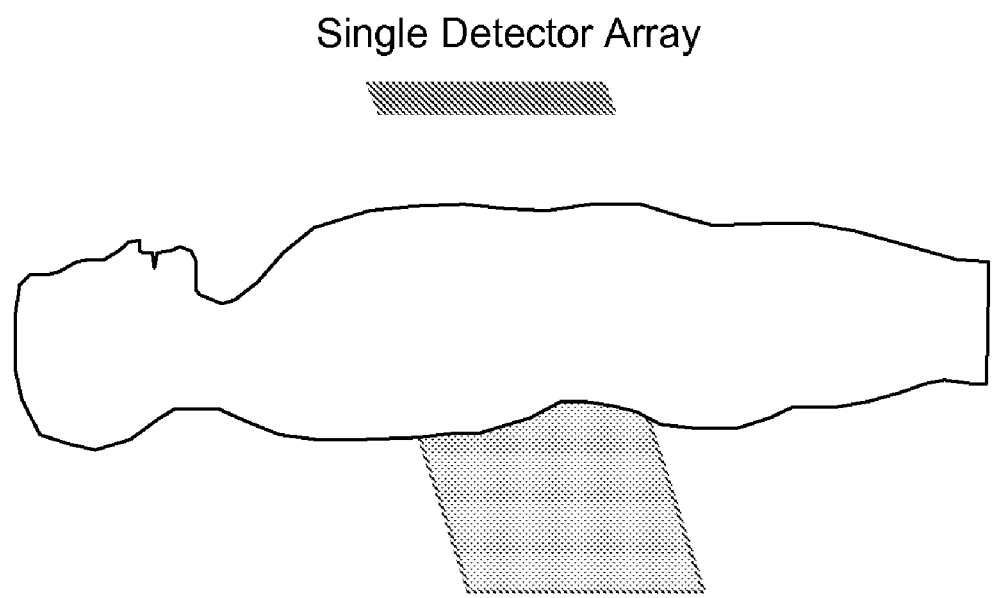
FIG. 1 is a depiction of an IGCT system with a large source array and small detector array.

An inverse geometry volumetric CT (IGCT) system uses a large-area scanned source and a 2D detector array with a smaller extent in the transverse direction. FIG. 1 is a depiction of this system with a large source array and small detector array. Because the source and detector have the same extent in the axial direction, the IGCT system can be immune from cone beam artifacts.

Figure 2:
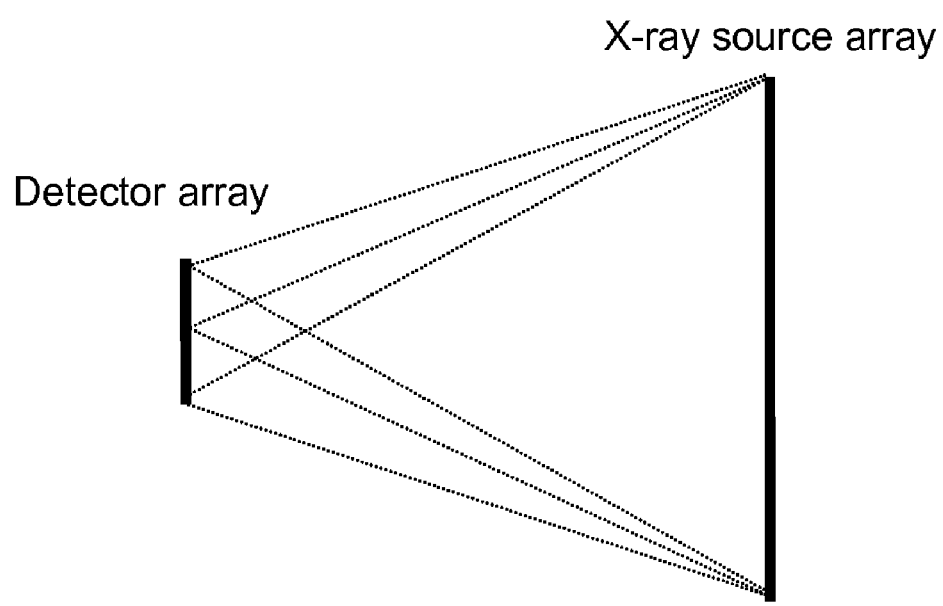
FIG. 2 is a transverse view of the IGCT system.

A reconstruction algorithm described in T. Gilat, R. Fahrig, N. Pelc, "Three-dimensional reconstruction algorithm for a reverse geometry volumetric CT system with a large array scanned source," in Medical Imaging 2003: Physics of Medical Imaging. Proc. SPIE 5030, pp. 103-111, 2003, for IGCT uses gridding to generate parallel ray data, and the gridding step can introduce blurring. An application of the present invention is a direct 2D IGCT reconstruction algorithm that does not require gridding. As will be further explained below, the transverse direction data set acquired by the IGCT system are very similar to that from a group of fan beams as can be seen in FIG. 2, which is a transverse view of an IGCT system. Therefore, an example of the invention provides an algorithm that relies on fan beam reconstruction and thereby can avoid the approximation inherent in gridding.

2D Transverse Section Example

Two systems were considered, their specifications are summarized in Table 1.

TABLE 1

Specifications for the two simulated IGCT systems

|  | System 1 | System 2 |
| --- | --- | --- |
| Source-to-Center-Detector distance | 100 cm | 100 cm |
| Source-to-Isocenter distance | 43.85 cm | 43.85 cm |
| Source array width | 25 cm | 25 cm |
| Detector array width | 0.625 cm, one sided | 2.5 cm, one sided |
| Source array spot spacing | 5 mm | 5 mm |
| Detector array element spacing | 0.3125 mm | 0.3125 mm |
| Source spot width | 0.5 mm | 0.5 mm |
| Number of 'Superviews' | 1000/360° | 278/360° |

As can be appreciated in FIG. 2, each individual IGCT detector element can be viewed as being the focal point of a fan beam view with ray paths connecting it to the sources. Each of these fan beams is at a slight different angle and a different radial alignment to the center of rotation. The IGCT system might have 20 detector elements in each row (e.g. system 1 in Table 1) and 50 x-ray focal spots in each row. Therefore, each 'superview' consists of 20 fan beam views. However, the source spot spacing (e.g. 5 mm) is much larger than the source spot size (e.g. 0.5 mm). Compared to a conventional fan beam system with one focal spot and 1000 detector elements, each of the views of the IGCT system is undersampled in the radial direction. This can be appreciated in FIGS. 3a-b which, in a simple case, compares a conventional fan beam with 8 detectors 304 and a single source 308 (FIG. 3a) to an IGCT system with 2 detectors 324a,b and 4 source spots 328 (FIG. 3b), where dotted lines represent missing rays in each undersampled IGCT fan beam.

Each ray from a source location to a detector location is described by two parameters, the signed distance between a ray and the isocenter, $\rho$, and the angle between the ray and the line from the source center to the isocenter, $\theta$. From FIG. 3b, it can be seen that in this case the fan beam view from one detector has only one half of the rho samples as compared to a full fan beam. It can also be seen however, that the fan beam view from the other detector provides additional rho samples. It is hypothesized that missing rho samples of the IGCT in one view can be compensated by other views, and that a high quality image could be obtained by using the data from all detectors.

In this example algorithm, each undersampled fan beam view is filtered and backprojected. It is necessary to ensure that the filtering step has enough bandwidth to retain the full system resolution. From Table 1, it can be seen that the source spacing is 10 times larger than the source spot width. Ideally, this ratio would be 0.5. Therefore, prior to filtering, 19 zeros were inserted between true source positions. Standard filtered-backprojection was then used. The filter was apodized with a Hanning filter. The angular rotation and offset alignment of each view was incorporated into the backprojection.

Computer Simulation

To evaluate this example reconstruction algorithm, analytical 2D uniform cylinders were simulated. Projection data were produced by calculating the path length of a given ray through the cylinder. Centered and off-centered objects were simulated. The simulated source row had 50 elements over 25 cm. In the first simulation, the simulated detector row had 20 elements over 0.625 cm, but the detector was mounted in an offset manner, with the ray from the center of the source array and passing through isocenter being aligned with the first detector. The simulation used 1000 superviews in 360°. The source and detector apertures were simulated by averaging projection data from discrete sub-sources and sub-detectors spanning the finite aperture sizes. Simulations were also performed for a system with 80 detectors (mounted off-center). Since this system has more rays per superview and the rays span a wider range of angles, only 278 superviews were used to adequately sample projection space.

Rho Gain Correction

Initial images of a 9 cm diameter centered cylinder had significant ring artifacts, as shown in FIGS. 4a-b. FIG. 4a is an image with ringing artifacts. FIG. 4b is a central profile in FIG. 4a. It is suspected that the ring artifacts are caused because the $\rho$ values of the IGCT rays are not exactly matched with those of a conventional fan-beam. This was confirmed by a comparison of the $\rho$ values of a fully sampled fan beam with those of an IGCT system with the same number of rays. There is a 'rho error' because the IGCT system has a different geometry than a fan beam system, and these rho errors cause the ringing artifacts seen in FIGS. 4a-b.

In this manifestation of the invention, the ringing artifacts from the rho errors are corrected by a pre-convolution sampling density compensation. This example of the invention finds weighting values (gain vector) for the IGCT data. The goal is to find a gain vector G such that when it is multiplied by the measured projection and reconstructed, an image comparable to the 2D fan beam reconstruction is produced.

The IGCT reconstruction includes the filtering and backprojection steps, and each step can be expressed as a matrix operation. If we have N-points of projection data per view and N-points of gain values corresponding to them, 2N−1 point filter coefficients are needed for the filtering step. P is defined as a projection data column vector, G as gain values, and H as a convolution matrix of filter coefficients. Then, the filtering F, can be conducted by the following matrix multiplication.

$$F = H*(P \cdot G) = \begin{bmatrix} h(0) & 0 & \ldots & 0 & 0 \\ . & h(0) & \ldots & . & . \\ . & . & \ldots & . & . \\ . & . & \ldots & 0 & . \\ h(2N-2) & . & \ldots & h(0) & 0 \\ 0 & h(2N-2) & \ldots & . & h(0) \\ . & 0 & \ldots & . & . \\ . & . & \ldots & . & . \\ . & . & \ldots & h(2N-2) & . \\ 0 & 0 & \ldots & 0 & h(2N-2) \end{bmatrix} \begin{bmatrix} p(0)g(0) \\ p(1)g(1) \\ p(2)g(2) \\ . \\ . \\ . \\ . \\ . \\ . \\ p(N-1)g(N-1) \end{bmatrix} \quad \text{(Equation 1)}$$

$$\begin{bmatrix} h(0)p(0) & 0 & \ldots & 0 & 0 \\ . & h(0)p(1) & \ldots & . & . \\ . & . & \ldots & . & . \\ . & . & \ldots & 0 & . \\ h(2N-2)p(0) & . & \ldots & h(0)p(N-2) & 0 \\ 0 & h(2N-2)p(1) & \ldots & . & h(0)p(N-1) \\ . & 0 & \ldots & . & . \\ . & . & \ldots & . & . \\ . & . & \ldots & h(2N-2)p(N-2) & . \\ 0 & 0 & \ldots & 0 & h(2N-2)p(N-1) \end{bmatrix} \begin{bmatrix} g(0) \\ g(1) \\ g(2) \\ . \\ . \\ . \\ . \\ . \\ . \\ g(N-1) \end{bmatrix} = A*G$$

Because pixel-driven backprojection with linear interpolation is used, a linear interpolation matrix L can be defined. Then, the reconstruction process, R_igct, can be expressed as a following matrix operation $$R\_igct = L*A*G \quad \text{(Equation 2)}$$

In equation 2, L and A are known values, and G is a vector of unknown gain values. In order to find gain vector G, R_igct was compared with the ideal fan beam reconstruction image R_fan. In both reconstructions, a large centered cylinder was used. An error vector E is defined as follows.

$$E = R\_igct - R\_fan \quad \text{(Equation 3)}$$

Then, the problem is simplified to find gain vector G which minimizes the error vector E. This was performed by using a conjugate-gradient method. An initial guess of the gain vector of all values equal to one was used in this example.

Once the gain vector is known, reconstruction of arbitrary data is performed by multiplying this gain vector by the IGCT projection data set prior to filtered backprojection. FIG. 4c shows the gain vector for the offset 20-detector geometry of Table 1, and FIG. 4d shows a central profile after applying the gain vector. The ringing artifacts were eliminated by the correction.

Result

Figure 5:
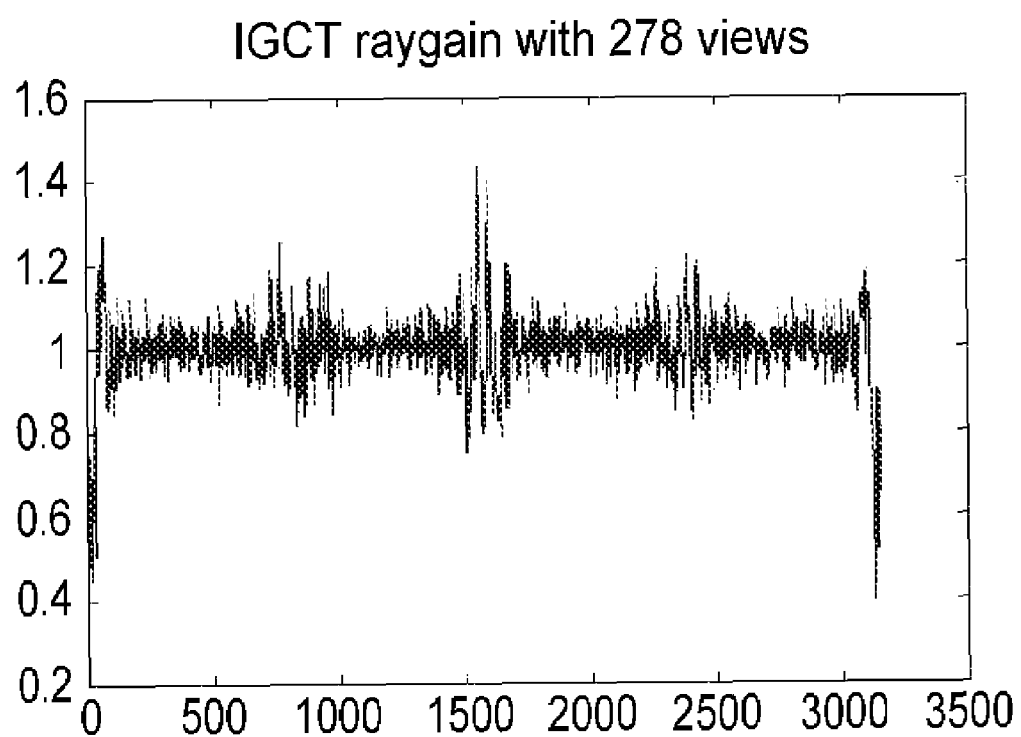
FIG. 5 shows the gain vector for the offset 80 detector IGCT system.

The IGCT geometry of system 1 in Table 1 has 0.24% rms rho error, and the ringing artifacts are corrected by the gain vector as shown in FIG. 4. FIG. 5 shows the gain vector for the 80 detector elements system. This system has 3160 rays per superview, and therefore needs a gain vector of 3160 values.

To explore the robustness of the 2D reconstruction algorithm in this example of the invention, an off-center uniform cylinder phantom was simulated. The cylinder had a radius of 3 cm and was centered at (1 cm, 1 cm). FIGS. 6a-d show the IGCT reconstructions without and with connection with the gain vector. FIG. 6a shows a reconstruction image before applying the gain vector. FIG. 6b shows a reconstruction image after applying the gain vector. FIG. 6c shows the central profile of the reconstruction image before applying the gain vector. FIG. 6d shows the central profile of the reconstruction image after applying the gain vector. Comparing the images, ringing artifacts are reduced to below 1 HU, and image does not show blurring.

CONCLUSIONS

This example of the invention provides a 2D IGCT reconstruction algorithm that does not require gridding. Because of the different geometry between the fan beam system and IGCT system, a gain correction is necessary, and a novel method to obtain the gain correction was developed. With this correction, ringing artifacts were reduced to within 1 HU.

Figure 7:
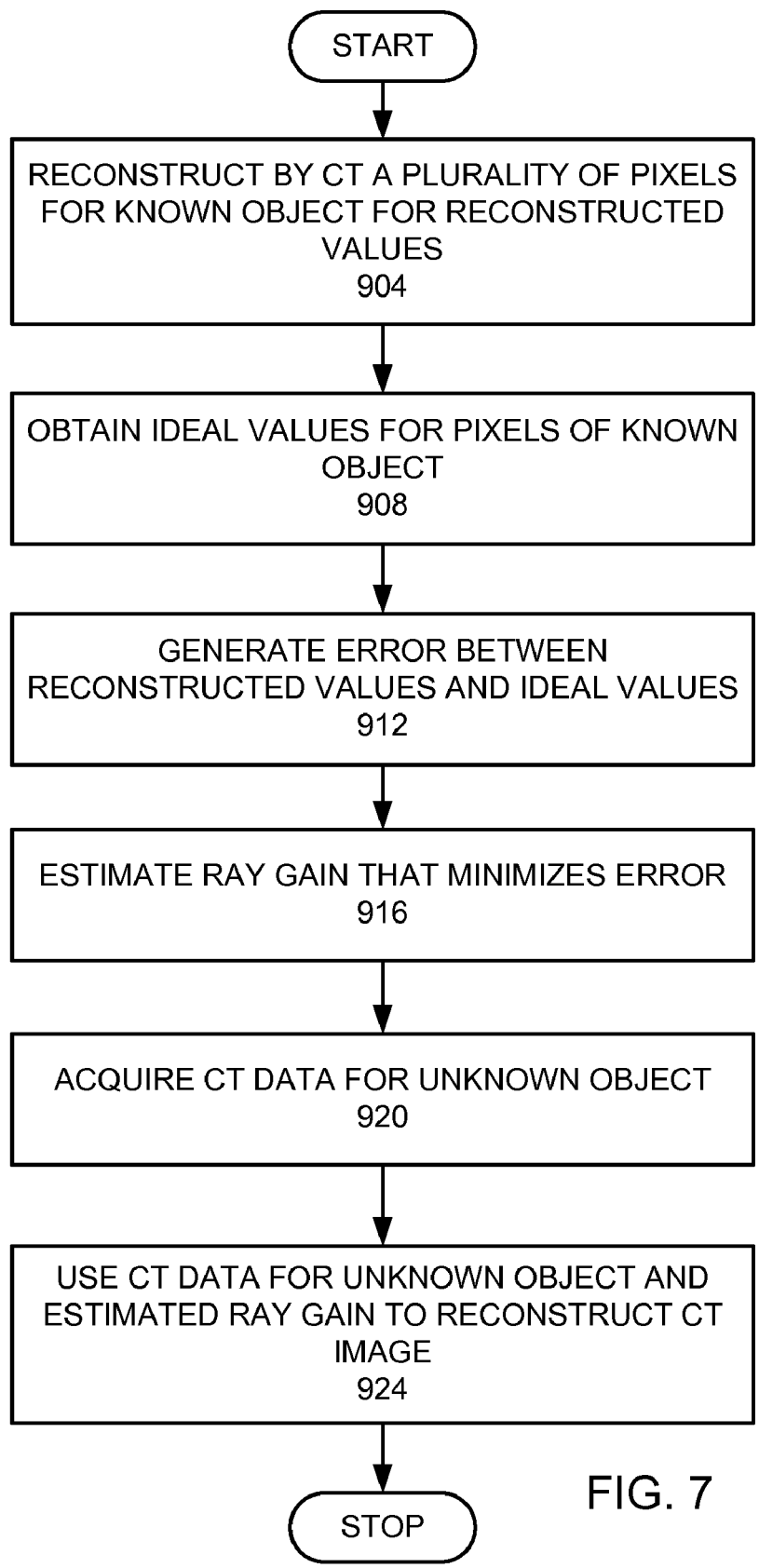
FIG. 7 is a flow chart of an embodiment of the invention.

This technique of determining a gain vector to reduce artifacts can have other application and embodiments. A generalized process is illustrated in FIG. 7. CT is used to reconstruct a plurality of pixels for a known object providing reconstructed values (step 904). Such a reconstruction may be for an entire image or parts of an image. The reconstruction may be two or three dimensional. Ideal pixel values for the known object are obtained (step 908). Such values may be obtained empirically, by simulation, or by other processes. An error is generated between the reconstructed values and the ideal values (step 912). Preferably, the error is related to the difference between the reconstructed values and the ideal values. The error related to the difference between the reconstructed values and ideal values may be root mean square (rms) differences, weighted differences, or differences with additional or alternative constraints.

A ray gain that minimizes the error is estimated (step 916). Such an estimation may use Newton's method to estimate the differential used to provide a minimization. From such an estimation a ray gain matrix may be determined.

CT data is acquired for an unknown object (step 920). The estimated ray gain is used with the acquired CT data for the unknown object to reconstruct a CT image (step 924).

Figure 8A:
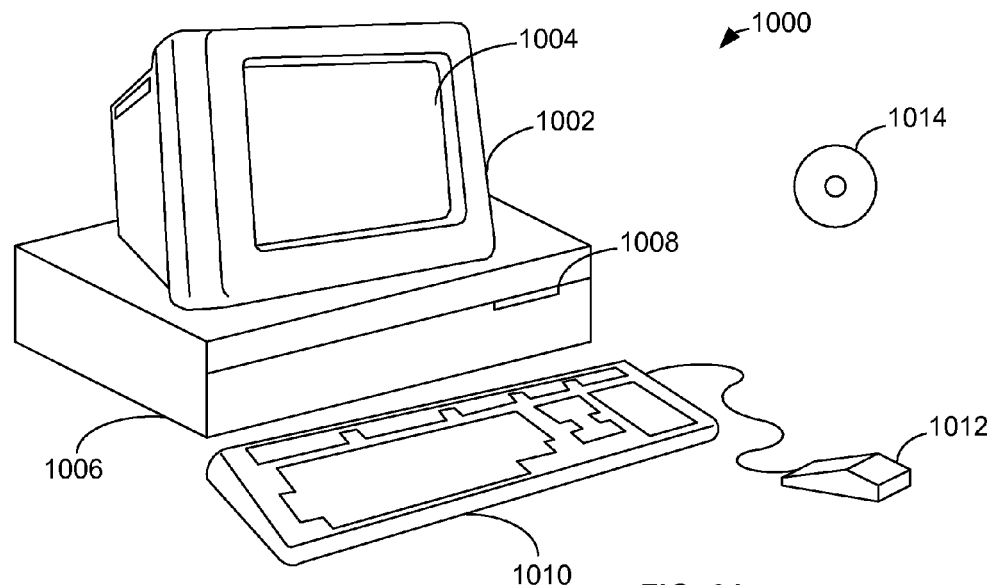
FIGS. 8A and 8B illustrate a computer system 1000, which is suitable for controlling an IGCT system in embodiments of the present invention.
Figure 8B:
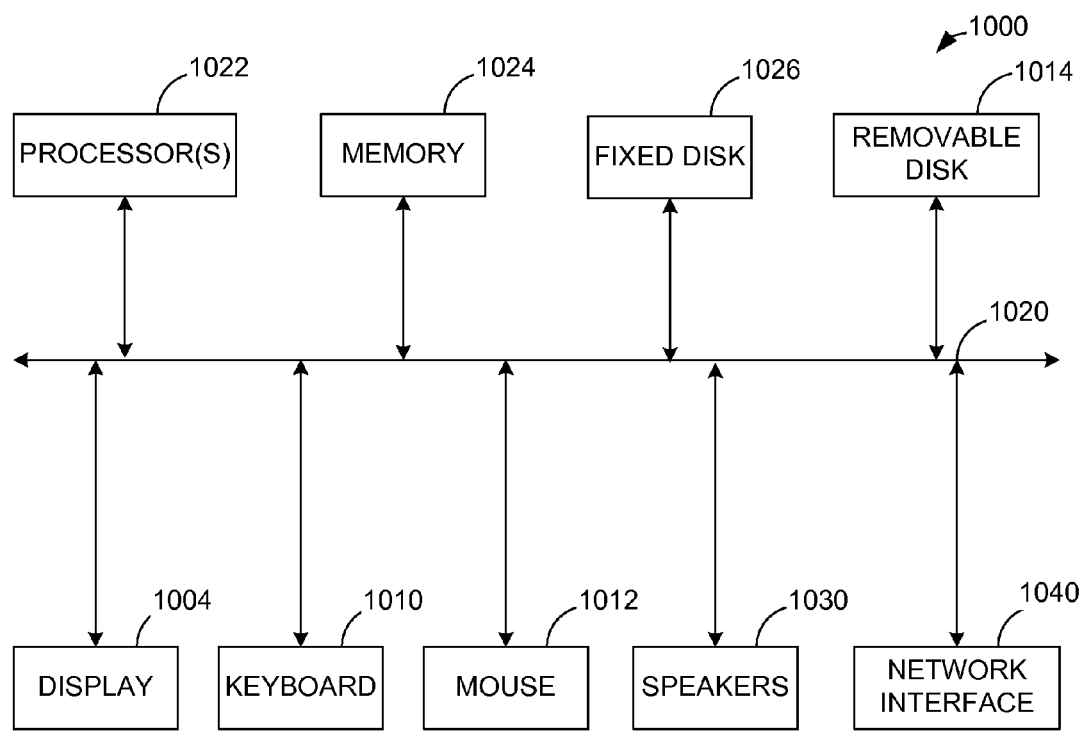

FIGS. 8A and 8B illustrate a computer system 1000, which is suitable for controlling an IGCT system in embodiments of the present invention. FIG. 8A shows one possible physical form of the computer system. Of course, the computer system may have many physical forms ranging from an integrated circuit, a printed circuit board, and a small handheld device up to a huge super computer. Computer system 1000 includes a monitor 1002, a display 1004, a housing 1006, a disk drive 1008, a keyboard 1010, and a mouse 1012. Disk 1014 is a computer-readable medium used to transfer data to and from computer system 1000.

FIG. 8B is an example of a block diagram for computer system 1000. Attached to system bus 1020 are a wide variety of subsystems. Processor(s) 1022 (also referred to as central processing units, or CPUs) are coupled to storage devices, including memory 1024. Memory 1024 includes random access memory (RAM) and read-only memory (ROM). As is well known in the art, ROM acts to transfer data and instructions uni-directionally to the CPU and RAM is used typically to transfer data and instructions in a bi-directional manner. Both of these types of memories may include any suitable of the computer-readable media described below. A fixed disk 1026 is also coupled bi-directionally to CPU 1022; it provides additional data storage capacity and may also include any of the computer-readable media described below. Fixed disk 1026 may be used to store programs, data, and the like and is typically a secondary storage medium (such as a hard disk) that is slower than primary storage. It will be appreciated that the information retained within fixed disk 1026 may, in appropriate cases, be incorporated in standard fashion as virtual memory in memory 1024. Removable disk 1014 may take the form of the computer-readable media described below.

CPU 1022 is also coupled to a variety of input/output devices, such as display 1004, keyboard 1010, mouse 1012, and speakers 1030. In general, an input/output device may be any of: video displays, track balls, mice, keyboards, microphones, touch-sensitive displays, transducer card readers, magnetic or paper tape readers, tablets, styluses, voice or handwriting recognizers, biometrics readers, or other computers. CPU 1022 optionally may be coupled to another computer or telecommunications network using network interface 1040. With such a network interface, it is contemplated that the CPU might receive information from the network, or might output information to the network in the course of performing the above-described method steps. Furthermore, method embodiments of the present invention may execute solely upon CPU 1022 or may execute over a network such as the Internet in conjunction with a remote CPU that shares a portion of the processing.

In addition, embodiments of the present invention further relate to computer storage products with a computer-readable medium that has computer code thereon for performing various computer-implemented operations. The media and computer code may be those specially designed and constructed for the purposes of the present invention, or they may be of the kind well known and available to those having skill in the computer software arts. Examples of computer-readable media include, but are not limited to: magnetic media such as hard disks, floppy disks, and magnetic tape; optical media such as CD-ROMs and holographic devices; magneto-optical media such as floptical disks; and hardware devices that are specially configured to store and execute program code, such as application-specific integrated circuits (ASICs), programmable logic devices (PLDs) and ROM and RAM devices. Examples of computer code include machine code, such as produced by a compiler, and files containing higher level code that are executed by a computer using an interpreter. Computer readable media may also be computer code transmitted by a computer data signal embodied in a carrier wave and representing a sequence of instructions that are executable by a processor.

It was unexpectedly found through a series of experiments that the estimated ray gain found for a known object would be useful in correcting a reconstructed image of an unknown and different object or an off-centered object.

Figure 3A:
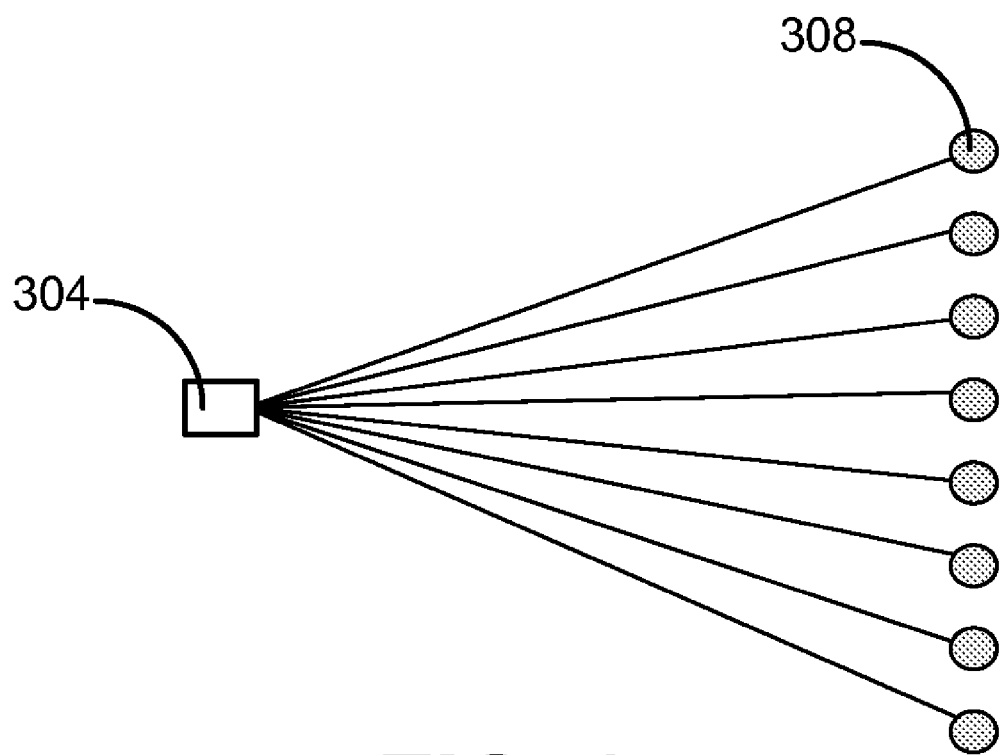
FIGS. 3a-b illustrate a simple case that compares a conventional fan beam with 8 detectors and a single source to an IGCT system with 2 detectors and 4 source spots 328, where dotted lines represent missing rays in each under sampled IGCT fan beam.
Figure 3B:
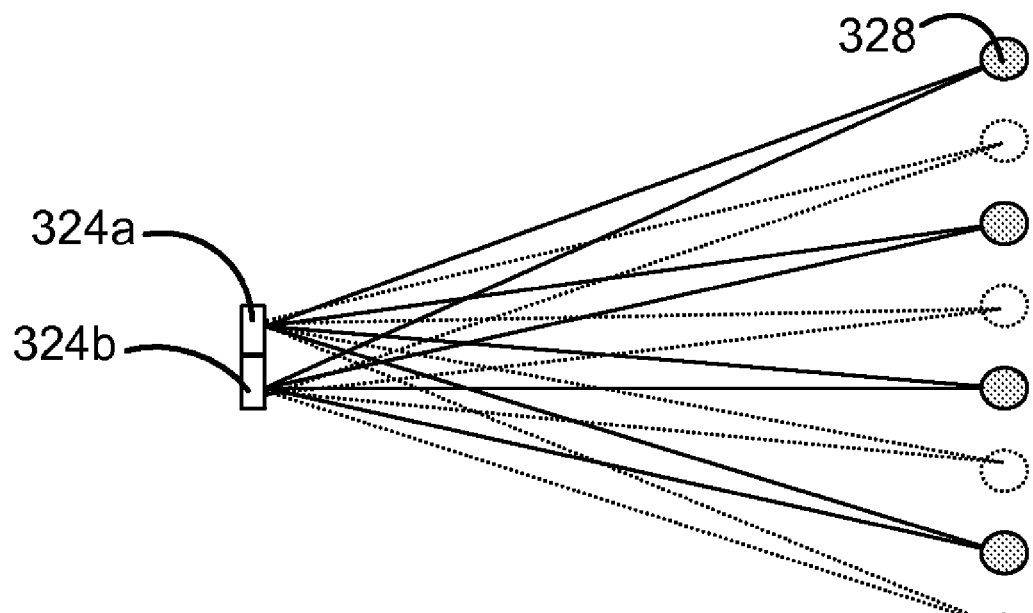

The above examples use an embodiment of the inventive process in an IGCT system for error caused by nonuniform rho sampling, such as a system shown in FIG. 3*b*, with multiple sources and detector elements. Other embodiments may be used for other error or for other system such as CT systems with a single source and multiple detector CT system, such as shown in FIG. 3*a*. For such systems, a computer system is used to perform ray gain estimation and reconstruction. Such a single source system may have different nonlinearities, gains, or errors in gain calculation.

Obtaining ideal values may be performed by a computer simulation or by empirically determining ideal values.

Because ideal values for pixels are reconstructed and compared, these embodiments of the invention compare final images instead of determining ray gain in projection space. Various embodiments may be used to weight values deemed to be more important. In other embodiments, additional constraints may be placed on the minimization of the error. For example, a constraint may be added, in addition minimizing the error, that keeps the gain values as close to one as possible. Such a constraint would avoid having one gain value that is very large and another gain value that is negative with a large absolute value While this invention has been described in terms of several preferred embodiments, there are alterations, permutations, modifications and various substitute equivalents, which fall within the scope of this invention. It should also be noted that there are many alternative ways of implementing the methods and apparatuses of the present invention. It is therefore intended that the following appended claims be interpreted as including all such alterations, permutations, modifications, and various substitute equivalents as fall within the true spirit and scope of the present invention.

What is claimed is:

1. A method for imaging unknown objects in a computed tomography (CT) system comprising at least one detector, at least one x-ray source, and a controller, wherein the controller executes the method comprising determining ray gain for a known object, comprising:
   a) performing CT reconstruction with the known object to obtain reconstructed values;
   b) obtaining ideal values for pixels of the known object;
   c) generating an error related to a difference between the reconstructed values and the ideal values; and
   d) estimating a ray gain that reduces the error.

2. The method, as recited in claim 1, wherein the controller executed method further comprises:
   acquiring CT data for the unknown object; and
   reconstructing a CT image of the unknown object by using the estimated ray gain.

3. The method, as recited in claim 2, wherein the reconstructing the CT image comprises using the equation R_fan=L*A*G, wherein R_fan is an ideal values of the fan beam reconstruction, A is a filtering matrix of the CT system, L is a back-projection matrix of the CT system, and G is the estimated ray gain.

4. The method, as recited in claim 3, wherein step c) generates the error using a root mean square (rms) difference between the reconstructed values and the ideal values.

5. The method, as recited in claim 3, wherein step c) generated the error using weighted differences between the reconstructed values and the ideal values.

6. The method, as recited in claim 3, wherein estimating the ray gain that minimizes the error also provides gain values as close to 1 as possible.

7. The method, as recited in claim 3, wherein reconstructing a CT image of the unknown object with the estimated ray gain does not use gridding.

8. The method, as recited in claim 7, wherein reconstructing a CT image of the unknown object with the estimated ray gain is performed by using a fan beam reconstruction algorithm.

9. The method, as recited in claim 2, wherein reconstructing a CT image of the unknown object with the estimated ray gain does not use gridding.

10. The method, as recited in claim 2, wherein reconstructing a CT image of the unknown object with the estimated ray gain is performed by using a fan beam reconstruction algorithm.

11. The method, as recited in claim 1, wherein step c) generates the error using a root mean square (rms) difference between the reconstructed values and the ideal values.

12. The method, as recited in claim 1, wherein step c) generated the error using weighted differences between the reconstructed values and the ideal values.

13. The method, as recited in claim 1, wherein estimating the ray gain that minimizes the error also provides gain values as close to 1 as possible.

14. A computed tomography (CT) system, comprising:
a detector array;
an x-ray source array;
a display;
a controller which receives data from the detector array and controls the display, comprising:
   at least one processor; and
   computer readable media, comprising:
     computer readable code for performing CT reconstruction with a known object to obtain reconstructed values;
     computer readable code for obtaining ideal values for pixels of the known object;
     computer readable code for generating an error related to a difference between the reconstructed values and the ideal values;
     computer readable code for estimating a ray gain that reduces the error;
     computer readable code for acquiring CT data for the unknown object;
     computer readable code for reconstructing a CT image of the unknown object by using the estimated ray gain; and
     computer readable code for displaying the CT image on the display.

15. The apparatus, as recited in claim 14, wherein the computer readable code for reconstructing the CT image comprises computer readable code for using the equation $R\_fan = L*A*G$, wherein $R\_fan$ is an ideal values of the fan beam reconstruction, A is a filtering matrix of the CT system, L is a back-projection matrix of the CT system, and G is the estimated ray gain.

16. The apparatus, as recited in claim 15, wherein the computer readable code for generating the error comprises computer readable code for generating the error using a root mean square (rms) difference between the reconstructed values and the ideal values.

17. The apparatus, as recited in claim 15, wherein the computer readable code for generating the error comprises computer readable code for generating the error using weighted differences between the reconstructed values and the ideal values.

18. The apparatus, as recited in claim 15, wherein computer readable code for estimating the ray gain that minimizes the error also provides gain values as close to 1 as possible.

19. The apparatus, as recited in claim 15, wherein the computer readable code for reconstructing a CT image of the unknown object with the estimated ray gain does not use gridding.

20. The apparatus, as recited in claim 15, wherein the computer readable code for reconstructing a CT image of the unknown object with the estimated ray gain comprises computer readable code for using a fan beam reconstruction algorithm.

* * * * *